United States Patent
Hart et al.

(10) Patent No.: US 10,748,646 B2
(45) Date of Patent: Aug. 18, 2020

(54) CHUNK-WISE TRANSMISSION OF TIME-SERIES DATA TO MOBILE DEVICES

(71) Applicant: General Electric Company, Schenectady, NY (US)

(72) Inventors: Michael Hart, San Ramon, CA (US); Milton Waid, San Ramon, CA (US); Jeremy Osterhoudt, San Ramon, CA (US); Andy Johns, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 673 days.

(21) Appl. No.: 15/395,136

(22) Filed: Dec. 30, 2016

(65) Prior Publication Data

US 2018/0189455 A1 Jul. 5, 2018

(51) Int. Cl.
*G06F 19/00* (2018.01)
*G16H 10/60* (2018.01)
*G16H 40/67* (2018.01)
*G16H 40/63* (2018.01)

(52) U.S. Cl.
CPC ............ *G16H 10/60* (2018.01); *G16H 40/63* (2018.01); *G16H 40/67* (2018.01)

(58) Field of Classification Search
CPC ........ G16H 40/63; G16H 10/60; G16H 40/67; H04L 65/4069; H04L 67/10; H04L 67/02; H04W 4/38
See application file for complete search history.

(56) References Cited

U.S. PATENT DOCUMENTS

| | | | | |
|---|---|---|---|---|
| 7,263,479 B2 * | 8/2007 | Cousins | ............... | H04L 63/045 704/205 |
| 9,921,869 B2 * | 3/2018 | Katsunuma | ....... | G06F 16/24568 |
| 2004/0059935 A1 * | 3/2004 | Cousins | ............... | H04L 63/045 726/12 |
| 2006/0110131 A1 * | 5/2006 | Okauchi | .............. | H04N 5/9202 386/252 |
| 2014/0241699 A1 * | 8/2014 | Honda | ............... | H04N 21/2401 386/248 |
| 2015/0199010 A1 * | 7/2015 | Coleman | ............. | A61B 5/0006 345/156 |
| 2015/0248446 A1 * | 9/2015 | Nordstrom | .............. | G06F 16/22 707/647 |
| 2016/0156948 A1 * | 6/2016 | Yang | ............. | H04N 21/234309 725/116 |
| 2016/0210338 A1 * | 7/2016 | Van Pelt | ............... | G06F 16/248 |
| 2016/0277475 A1 * | 9/2016 | Lee | .......................... | H04L 65/80 |
| 2017/0076206 A1 * | 3/2017 | Lastras-Montano | ........................ | G06F 16/3344 |
| 2017/0103103 A1 * | 4/2017 | Nixon | .................... | G06F 16/256 |
| 2017/0329828 A1 * | 11/2017 | Gupta | ................. | G06F 16/9535 |
| 2018/0063213 A1 * | 3/2018 | Bevilacqua-Linn | ........................ H04L 65/605 |

* cited by examiner

*Primary Examiner* — Abdullahi E Salad
(74) *Attorney, Agent, or Firm* — Buckley, Maschoff & Talwalkar LLC

(57) ABSTRACT

A computer receives a stream of time-series data from a data generating device. The computer converts the stream of time-series data into a sequence of chunks. The chunks are transmitted from the computer to a mobile device. The transmitting is on a chunk-by-chunk basis and in response to an indication by the mobile device that it is available to receive the next chunk from the sequence of chunks.

5 Claims, 9 Drawing Sheets

CHUNK-WISE TRANSMISSION OF TIME-SERIES DATA TO MOBILE DEVICES

BACKGROUND

Industrial and other complex machine equipment or assets may be engineered to perform particular tasks as part of industrial, manufacturing, monitoring or business processes. For example, industrial assets can include, among other things and without limitation, manufacturing equipment on a production line, wind turbines that generate electricity on a wind farm, healthcare or imaging devices (e.g., X-ray or MRI systems) or patient monitoring devices for use in patient care facilities, or drilling equipment for use in mining operations. The design and implementation of these assets often takes into account both the physics of the task at hand, as well as the environment in which such assets are configured to operate.

Low-level software and hardware-based controllers have long been used to configure, operate and monitor these assets. However, the rise of inexpensive cloud computing, increasing sensor capabilities, and decreasing sensor costs, as well as the proliferation of mobile technologies have created opportunities for creating novel industrial assets with improved sensing technology that are capable of transmitting data that can then be transmitted to a network. As a consequence, there are many new opportunities to enhance the value of some industrial assets using novel industrial-focused hardware and software.

One important aspect of the use of data generated by industrial assets and other types of devices is that the data may be distributed to mobile devices (e.g., smartphones, tablet computers) carried by individuals who are "on the go" but need or wish to be kept up to date on the data produced or stored in a network. Previous proposals for distributing data from central data repositories have often assumed that devices intended to receive the data from a central source are connected to the central source by reliable and substantially uninterrupted communication channels. However that assumption may not hold if mobile devices are to be the recipients of the data, particularly where the users of such devices may be in the field and subject to intermittent mobile network connectivity. In other words, transmitting streams of data to mobile devices from central data repositories present problems, as well as opportunities, not involved with data distribution to reliably-connected devices.

DETAILED DESCRIPTION

Figure 1:
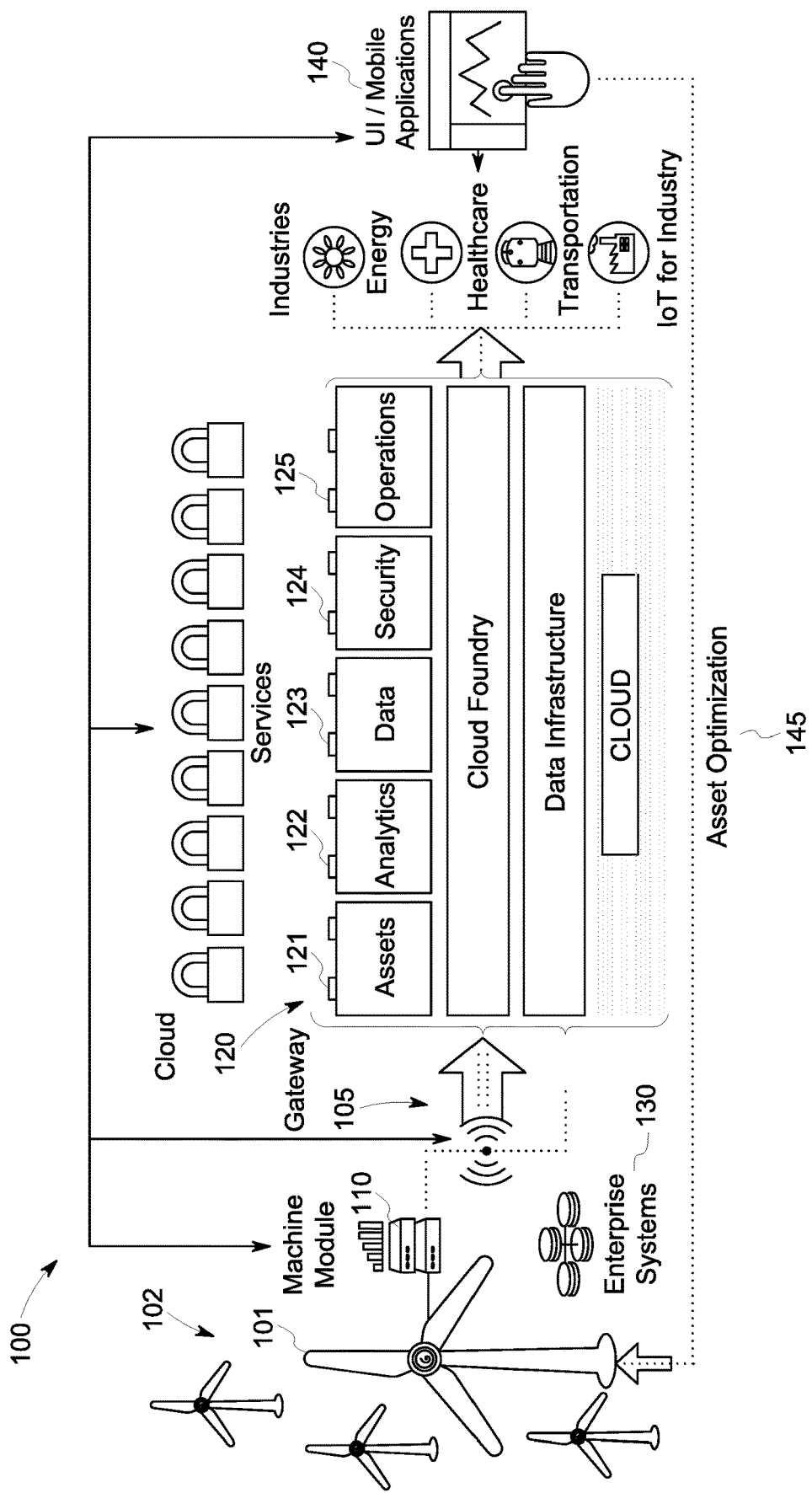
FIG. 1 illustrates generally an example of portions of a first asset management platform (AMP).

While progress with industrial and other complex equipment automation has been made over the last several decades, and assets have become "smarter," the intelligence of any individual asset pales in comparison to intelligence that can be gained when multiple smart devices are connected together. Aggregating data collected from or about multiple assets can enable users to improve business processes, for example by improving effectiveness of asset maintenance or improving operational performance if appropriate industrial-specific data collection and modeling technology is developed and applied. Improvements may also be made in making a unified set of data available in a timely manner to individuals who are involved with organizational processes while traveling from place to place.

In an example, an industrial asset can be outfitted with one or more sensors configured to monitor respective ones of an asset's operations or conditions. Data from the one or more sensors can be recorded or transmitted to a cloud-based or other remote computing environment. By bringing such data into a cloud-based computing environment, new software applications informed by industrial process, tools and know-how can be constructed, and new physics-based analytics specific to an industrial environment can be created. Insights gained through analysis of such data can lead to enhanced asset designs, or to enhanced software algorithms for operating the same or similar asset at its edge, that is, at the extremes of its expected or available operating conditions.

The systems and methods for managing industrial assets can include or can be a portion of an Industrial Internet of Things (IIoT). In an example, an IIoT connects industrial assets, such as wind turbines, gas turbines, jet engines, and locomotives, to the Internet or cloud, or to each other in some meaningful way. The systems and methods described herein can include using a "cloud" or remote or distributed computing resource or service. The cloud can be used to receive, relay, transmit, store, analyze, or otherwise process information for or about one or more industrial assets. In an example, a cloud computing system includes at least one processor circuit, at least one database, and a plurality of users or assets that are in data communication (continuously or from time to time) with the cloud computing system. The cloud computing system can further include or can be coupled with one or more other processor circuits or modules configured to perform a specific task, such as to perform tasks related to asset maintenance, analytics, data storage, data exchange, security, health care delivery or monitoring, or some other function.

However, the integration of industrial assets with the remote computing resources to enable the IIoT often presents technical challenges separate and distinct from the specific industry and from computer networks, generally. A given industrial asset may need to be configured with novel interfaces and communication protocols to send and receive data to and from distributed computing resources. Given industrial assets may have strict requirements for cost, weight, security, performance, signal interference, and the like such that enabling such an interface is rarely as simple as combining the industrial asset with a general purpose computing device.

To address these problems and other problems resulting from the intersection of certain industrial fields and the IIoT, embodiments may enable improved interfaces, techniques, protocols, and algorithms for facilitating communication with and configuration of industrial assets via remote computing platforms and frameworks. Improvements in this regard may relate to both improvements that address particular challenges related to particular industrial assets (e.g., improved aircraft engines, wind turbines, locomotives, medical imaging equipment) that address particular problems related to use of these industrial assets with these remote computing platforms and frameworks, and also improvements that address challenges related to operation of the platform itself to provide improved mechanisms for configuration, analytics, and remote management of industrial assets as well as distribution of resulting data to individuals who work with or need data generated by industrial assets.

The Predix™ platform available from GE is a novel embodiment of such Asset Management Platform (AMP) technology enabled by state of the art cutting edge tools and cloud computing techniques that enable incorporation of a manufacturer's asset knowledge with a set of development tools and best practices that enables asset users to bridge gaps between software and operations to enhance capabilities, foster innovation, and ultimately provide economic value. Through the use of such a system, a manufacturer of industrial assets can be uniquely situated to leverage its understanding of industrial assets themselves, models of such assets, and industrial operations or applications of such assets, to create new value for industrial customers through asset insights.

FIG. 1 illustrates generally an example of portions of a first AMP 100. As further described herein, one or more portions of an AMP can reside in an asset cloud computing system 120, in a local or sandboxed environment, or can be distributed across multiple locations or devices. An AMP can be configured to perform any one or more of data acquisition, data analysis, or data exchange with local or remote assets, or with other task-specific processing devices.

The first AMP 100 includes a first asset community 102 that is communicatively coupled with the asset cloud computing system 120. In an example, a machine module 110 receives information from, or senses information about, at least one asset member of the first asset community 102, and configures the received information for exchange with the asset cloud computing system 120. In an example, the machine module 110 is coupled to the asset cloud computing system 120 or to an enterprise computing system 130 via a communication gateway 105.

In an example, the communication gateway 105 includes or uses a wired or wireless communication channel that extends at least from the machine module 110 to the asset cloud computing system 120. The asset cloud computing system 120 includes several layers. In an example, the asset cloud computing system 120 includes at least a data infrastructure layer, a cloud foundry layer, and modules for providing various functions. In the example of FIG. 1, the asset cloud computing system 120 includes an asset module 121, an analytics module 122, a data acquisition module 123, a data security module 124, and an operations module 125. (In some embodiments, the asset cloud computing system may also include a data distribution module—not separately shown—which may at least partially overlap with the data acquisition module 123.) Each of the modules 121-125 includes or uses a dedicated circuit, or instructions for operating a general purpose processor circuit, to perform the respective functions. In an example, the modules 121-125 are communicatively coupled in the asset cloud computing system 120 such that information from one module can be shared with another. In an example, the modules 121-125 are co-located at a designated datacenter or other facility, or the modules 121-125 can be distributed across multiple different locations.

An interface device 140 can be configured for data communication with one or more of the machine module 110, the gateway 105, or the asset cloud computing system 120. The interface device 140 can be used to monitor or control one or more assets. In an example, information about the first asset community 102 is presented to an operator at the interface device 140. The information about the first asset community 102 can include information from the machine module 110, or the information can include information from the asset cloud computing system 120. In an example, the information from the asset cloud computing system 120 includes information about the first asset community 102 in the context of multiple other similar or dissimilar assets, and the interface device 140 can include options for optimizing one or more members of the first asset community 102 based on analytics performed at the asset cloud computing system 120.

In an example, an operator selects a parameter update for the first wind turbine 101 using the interface device 140, and the parameter update is pushed to the first wind turbine via one or more of the asset cloud computing system 120, the gateway 105, and the machine module 110. In an example, the interface device 140 is in data communication with the enterprise computing system 130 and the interface device 140 provides an operation with enterprise-wide data about the first asset community 102 in the context of other business or process data. For example, choices with respect to asset optimization can be presented to an operator in the context of available or forecasted raw material supplies or fuel costs. In an example, choices with respect to asset optimization can be presented to an operator in the context of a process flow to identify how efficiency gains or losses at one asset can impact other assets. In an example, one or more choices described herein as being presented to a user or operator can alternatively be made automatically by a processor circuit according to earlier-specified or programmed operational parameters. In an example, the processor circuit can be located at one or more of the interface device 140, the asset cloud computing system 120, the enterprise computing system 130, or elsewhere.

Returning again to the example of FIG. 1, some capabilities of the first AMP 100 are illustrated. The example of FIG. 1 includes the first asset community 102 with multiple wind turbine assets, including the first wind turbine 101. Wind turbines are used in some examples herein as non-limiting examples of a type of industrial asset that can be a part of, or in data communication with, the first AMP 100.

In an example, the multiple turbine members of the asset community 102 include assets from different manufacturers or vintages. The multiple turbine members of the asset community 102 can belong to one or more different asset communities, and the asset communities can be located locally or remotely from one another. For example, the members of the asset community 102 can be colocated on a single wind farm, or the members can be geographically distributed across multiple different farms. In an example, the multiple turbine members of the asset community 102 can be in use (or non-use) under similar or dissimilar environmental conditions, or can have one or more other common or distinguishing characteristics.

FIG. 1 further includes the device gateway 105 configured to couple the first asset community 102 to the asset cloud computing system 120. The device gateway 105 can further couple the asset cloud computing system 120 to one or more other assets or asset communities, to the enterprise computing system 130, or to one or more other devices, including mobile devices, as discussed below. The first AMP 100 thus represents a scalable industrial solution that extends from a physical or virtual asset (e.g., the first wind turbine 101) to a remote asset cloud computing system 120. The asset cloud computing system 120 optionally includes a local, system, enterprise, or global computing infrastructure that can be optimized for industrial data workloads, secure data communication, and compliance with regulatory requirements.

In an example, information from an asset, about the asset, or sensed by an asset itself is communicated from the asset to the data acquisition module 124 in the asset cloud computing system 120. In an example, an external sensor can be used to sense information about a function of an asset, or to sense information about an environment condition at or near an asset. The external sensor can be configured for data communication with the device gateway 105 and the data acquisition module 124, and the asset cloud computing system 120 can be configured to use the sensor information in its analysis of one or more assets, such as using the analytics module 122.

In an example, the first AMP 100 can use the asset cloud computing system 120 to retrieve an operational model for the first wind turbine 101, such as using the asset module 121. The model can be stored locally in the asset cloud computing system 120, or the model can be stored at the enterprise computing system 130, or the model can be stored elsewhere. The asset cloud computing system 120 can use the analytics module 122 to apply information received about the first wind turbine 101 or its operating conditions (e.g., received via the device gateway 105) to or with the retrieved operational model. Using a result from the analytics module 122, the operational model can optionally be updated, such as for subsequent use in optimizing the first wind turbine 101 or one or more other assets, such as one or more assets in the same or different asset community. For example, information about the first wind turbine 101 can be analyzed at the asset cloud computing system 120 to inform selection of an operating parameter for a remotely located second wind turbine that belongs to a different second asset community.

The first AMP 100 includes a machine module 110. The machine module 110 includes a software layer configured for communication with one or more industrial assets and the asset cloud computing system 120. In an example, the machine module 110 can be configured to run an application locally at an asset, such as at the first wind turbine 101. The machine module 110 can be configured for use with or installed on gateways, industrial controllers, sensors, and other components. In an example, the machine module 110 includes a hardware circuit with a processor that is configured to execute software instructions to receive information about an asset, optionally process or apply the received information, and then selectively transmit the same or different information to the asset cloud computing system 120.

In an example, the asset cloud computing system 120 can include the operations module 125. The operations module 125 can include services that developers can use to build or test Industrial Internet applications, or the operations module 125 can include services to implement Industrial Internet applications, such as in coordination with one or more other AMP modules. In an example, the operations module 125 includes a microservices marketplace where developers can publish their services and/or retrieve services from third parties. The operations module 125 can include a development framework for communicating with various available services or modules. The development framework can offer developers a consistent look and feel and a contextual user experience in web or mobile applications.

In an example, an AMP can further include a connectivity module. The connectivity module can optionally be used where a direct connection to the cloud is unavailable. For example, a connectivity module can be used to enable data communication between one or more assets and the cloud using a virtual network of wired (e.g., fixed-line electrical, optical, or other) or wireless (e.g., cellular, satellite, or other) communication channels. In an example, a connectivity module forms at least a portion of the gateway 105 between the machine module 110 and the asset cloud computing system 120, and/or between the asset cloud computing system 120 and other components of the AMP 100, including for example mobile devices (as discussed below) and/or fixed-location data-receiving devices.

In an example, an AMP can be configured to aid in optimizing operations or preparing or executing predictive maintenance for industrial assets. An AMP can leverage multiple platform components to predict problem conditions and conduct preventative maintenance, thereby reducing unplanned downtimes. In an example, the machine module 110 is configured to receive or monitor data collected from one or more asset sensors and, using physics-based analytics (e.g., finite element analysis or some other technique selected in accordance with the asset being analyzed), detect error conditions based on a model of the corresponding asset. In an example, a processor circuit applies analytics or algorithms at the machine module 110 or at the asset cloud computing system 120.

In response to the detected error conditions, the AMP can issue various mitigating commands to the asset, such as via the machine module 110, for manual or automatic implementation at the asset. In an example, the AMP can provide a shut-down command to the asset in response to a detected error condition. Shutting down an asset before an error condition becomes fatal can help to mitigate potential losses or to reduce damage to the asset or its surroundings. In addition to such an edge-level application, the machine module 110 can communicate asset information to the asset cloud computing system 120.

In an example, the asset cloud computing system 120 can store or retrieve operational data for multiple similar assets. Over time, data scientists or machine learning can identify patterns and, based on the patterns, can create improved physics-based analytical models for identifying or mitigating issues at a particular asset or asset type. The improved analytics can be pushed back to all or a subset of the assets, such as via multiple respective machine modules 110, to effectively and efficiently improve performance of designated (e.g., similarly-situated) assets.

In an example, the asset cloud computing system 120 includes a Software-Defined Infrastructure (SDI) that serves as an abstraction layer above any specified hardware, such as to enable a data center to evolve over time with minimal disruption to overlying applications. The SDI enables a shared infrastructure with policy-based provisioning to facilitate dynamic automation, and enables SLA (service level agreement) mappings to underlying infrastructure. This configuration can be useful when an application requires an underlying hardware configuration. The provisioning management and pooling of resources can be done at a granular level, thus allowing optimal resource allocation.

In a further example, the asset cloud computing system 120 is based on Cloud Foundry (CF), an open source PaaS (Platform-as-a-Service) that supports multiple developer frameworks and an ecosystem of application services. Cloud Foundry can make it faster and easier for application developers to build, test, deploy, and scale applications. Developers thus gain access to the vibrant CF ecosystem and an ever-growing library of CF services. Additionally, because it is open source, CF can be customized for IIoT workloads.

The asset cloud computing system 120 can include a data services module that can facilitate application development. For example, the data services module can enable developers to bring data into the asset cloud computing system 120 and to make such data available for various applications, such as applications that execute at the cloud, at a machine module, or at an asset or other location (such as a mobile device). In an example, the data services module can be configured to cleanse, merge, or map data before ultimately storing it in an appropriate data store, for example, at the asset cloud computing system 120. A special emphasis has been placed on time-series data, as it is the data format that most sensors use. In an example, and as discussed further below, time-series data may be converted to a form in which it is more suitable for distribution to mobile devices.

Security can be a concern for data services that deal in data exchange between the asset cloud computing system 120 and one or more assets or other components. Some options for securing data transmissions include using Virtual Private Networks (VPNs) or an SSL/TLS (secure socket layer/transport layer security) model. In an example, the first AMP 100 can support two-way TLS, such as between a machine module and the security module 124. In an example, two-way TLS may not be supported, and the security module 124 can treat client devices as OAuth users. For example, the security module 124 can allow enrollment of an asset (or other device) as an OAuth client and transparently use OAuth access tokens to send data to protected endpoints.

In some examples, a time-series data stream may be converted to data "chunks" at the asset cloud computing system 120 so as to more readily accommodate the needs of mobile devices to which the data is to be sent. The converted time-series data may be sent chunk-by-chunk in response to per-chunk requests from recipient mobile devices. Index marks (including alarm/alert condition notations, annotations received from other mobile devices that are common recipients of the time-series data, etc.) may be inserted in the data stream prior to conversion to make the data more useful/user-friendly for the users of the recipient mobile devices. As used herein and in the appended claims, a "chunk" or "data chunk" refers to a unit of information that has been suitably packaged to support asynchronous, interrupted or by-demand distribution of the information.

Figure 2:
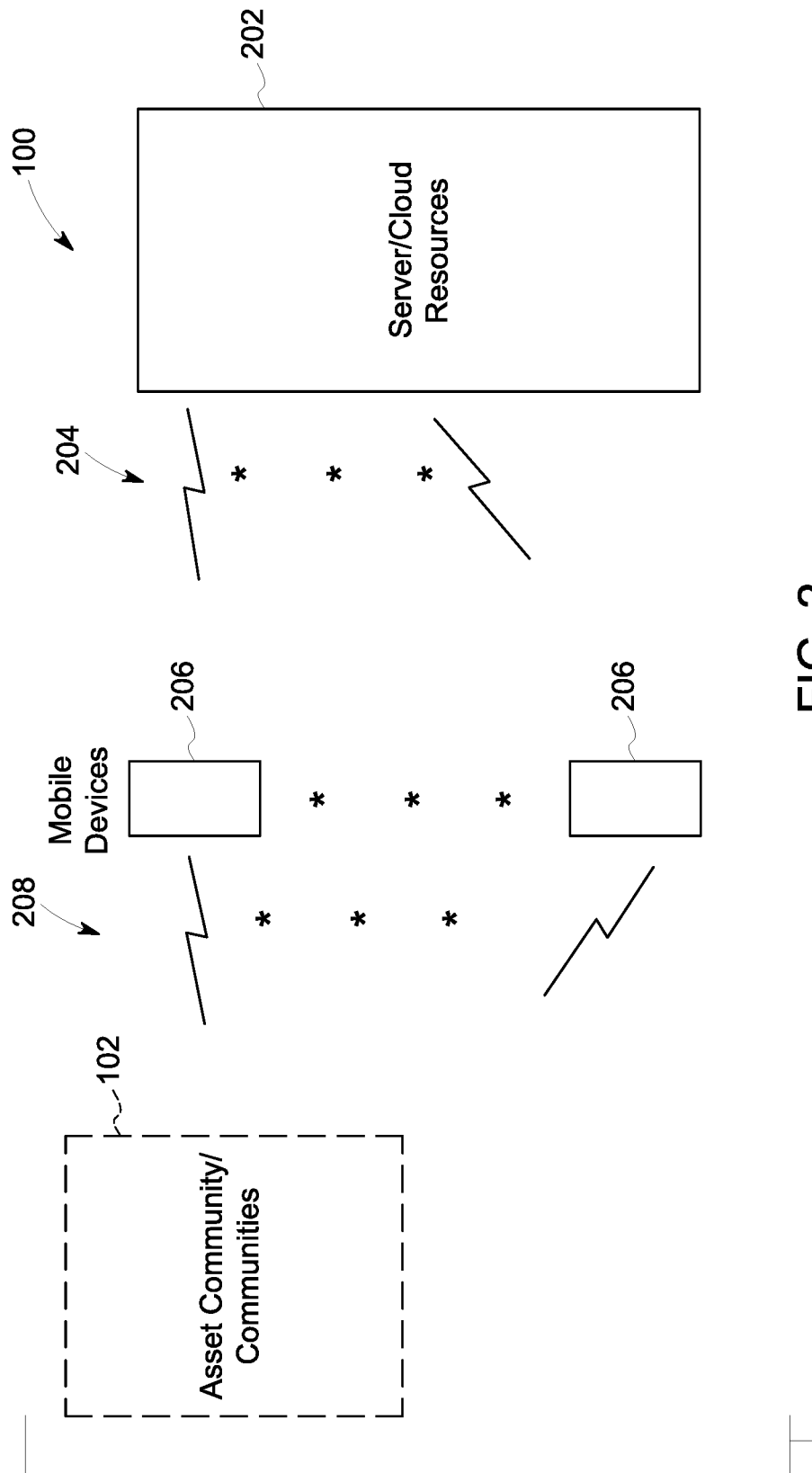
FIGS. 2, 3, 4 and 5 are high level block diagrams showing other aspects of the AMP depicted in FIG. 1.

FIG. 2 is a high level block diagram showing other aspects of the AMP 100 depicted in FIG. 1.

As seen from FIG. 2, the AMP 100 may include a central source of data, labeled in the drawing as a server or one or more cloud computing resources and indicated by reference numeral 202. From prior discussion, it will be appreciated that the server/computing resource 202 may be all or part of the asset cloud computing system 120 or the enterprise systems 130 shown in FIG. 1 or may be another computing device or type of computing device.

As indicated schematically at 204 in FIG. 2, the server 202 may distribute data via wireless communications to numerous mobile devices 206. The communication channel(s) between the server 202 and the mobile devices 206 (which communication channels are not explicitly shown in the drawing) may include, for example, one or more mobile communication networks, as well as other communication networks such as the internet and/or one or more private networks and/or VPNs (virtual private networks). The above discussion of direct or other sorts of connectivity to the AMP is also pertinent.

In an example, all the data provided from the server 202 to the mobile devices 206 may be provided essentially for the purpose of providing an information feed to users (not shown) of the mobile devices. In an example, the mobile device users may be medical personnel who receive from the server 202 feeds of data generated by (or of data generated from analysis of data generated by) medical monitoring devices that sense vital signs and other indicators of the current and changing conditions of hospitalized patients. It will be understood, in connection with this example, that the medical monitoring devices (though not explicitly depicted in FIG. 1 or FIG. 2) are to be considered among the assets of the AMP 100 as presented in FIG. 1.

In another example, the data fed from the server 202 to the mobile devices 206 may include operational indicators of assets of the AMP so that the users of the mobile devices 206 may be prompted to perform tasks relative to the assets such as visual inspections, mechanical tests and/or adjustments, setting of local control mechanisms for the assets, emergency shut-down procedures, rebooting of local electronic controllers, etc. The types of assets referred to in the previous sentence may include wind turbines, locomotives, jet engines, large pieces of medical diagnostic equipment, factory production equipment, power generation equipment (e.g., gas turbines) that consumes fossil fuel to generate electricity, etc.

In an example, the server 202 (e.g., assuming it to include resources of the asset cloud computing system 120) may simultaneously deliver two or more different types of the data feeds referred to above to mobile devices employed by two, three or more different organizations/enterprises. In an example, the server 202 provides respective data feeds to numerous mobile devices 206 simultaneously or virtually simultaneously. In some examples, the same data feed may be provided simultaneously to a group of mobile devices 206 carried by individuals who share a common interest in the particular data feed. Returning, for example, to the medical monitoring example, several doctors or other medical professionals responsible for treating a certain patient may all receive the same feed of medical monitoring data for that patient. That feed may be received at the users' mobile devices interspersed with other data feeds containing medical monitoring data for other patients. The members of the above-mentioned group of medical professionals may receive over-all feeds that reflect the medical monitoring of different respective groups of patients, given that different professionals may be charged with caring for different groups of patients.

It may also be the case, where the data feeds represent asset operational indicators, that there may be groups of individuals who receive duplicate feeds for assets for which they share responsibility. At the same time, as in the medical example, some members of the group may receive data feeds for other assets that only they are responsible for, and the latter feeds may not be provided to members of the group not responsible for the last-mentioned assets.

In an example, as indicated schematically at 208, at least some of the mobile devices 206 may communicate data and/or control signals to assets in one or more asset communities 102. In an example, the communication from the mobile devices 206 may be via one or more machine modules 110 (per the above discussion of FIG. 1; machine module(s) not shown in FIG. 2). In an example, a mobile device 206 may simply relay data that it has received from the server 202 to an asset; the communication from the mobile device 206 to the asset may be via short-range radio communications, in some example. In another example, the mobile device 206 may, via an application program running in the mobile device, process data received from the server 202 to generate processed data and/or one or more control signals, which are in turn (processed data and/or control signals) communicated from the mobile device 206 to one or more assets. The asset(s) receiving the processed data/control signals from the mobile device 206 may be one or more of the types of AMP assets referred to above.

The communication channel(s) between the mobile devices 206 and the asset(s) (which communication channels are not explicitly shown in the drawing) need not be short-range communication channels. The communication channels between the mobile devices 206 and the asset(s) may include, for example, one or more mobile communication networks, as well as other communication networks such as the internet and/or one or more private networks and/or VPNs (virtual private networks).

In cases where the asset has a short-range data communication capability suitable for providing a communication channel to a nearby mobile device 206, the mobile device and the asset's short range communication capability may provide a backup channel in the event that normal communication channels between the asset and the asset cloud computing system 120 suffer an outage.

Figure 3:
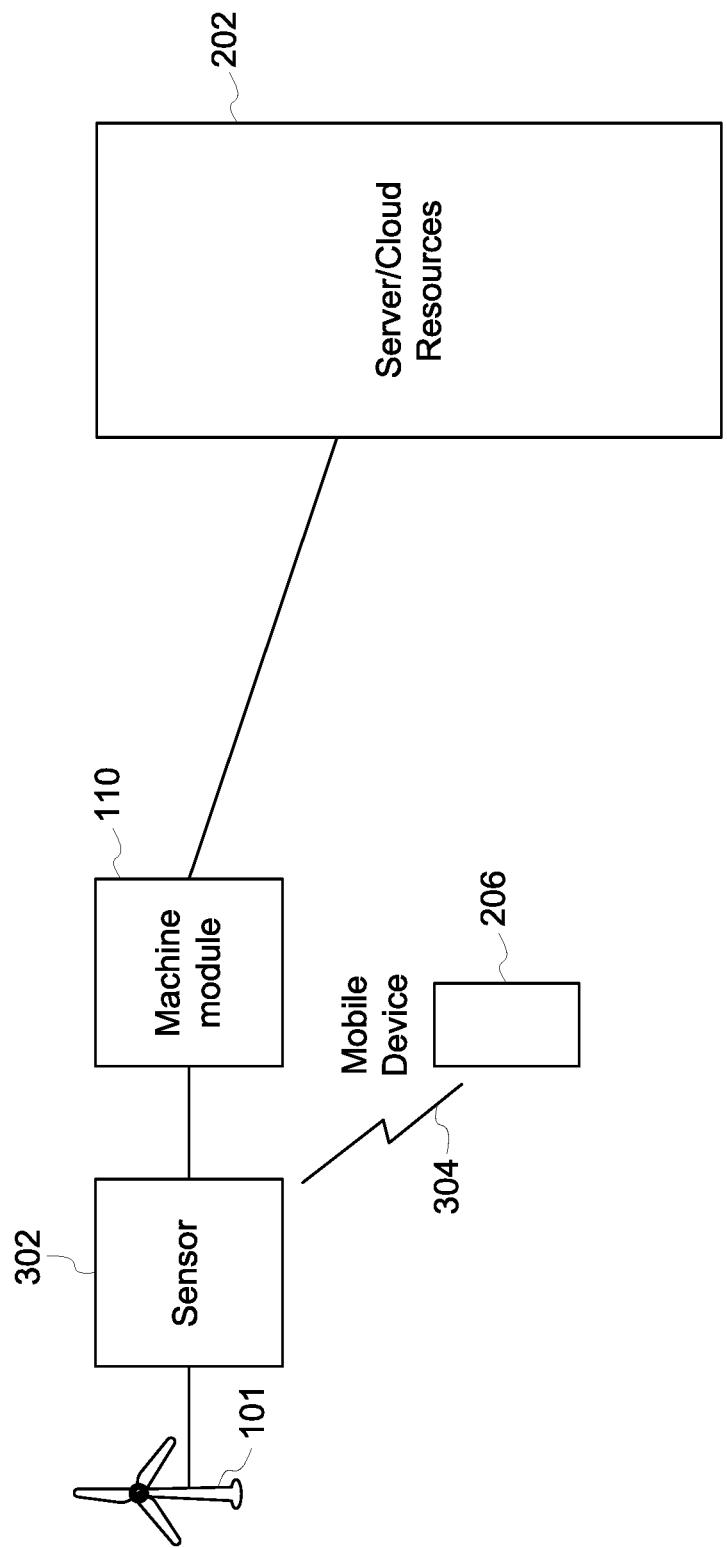

FIG. 3 is a high level block diagram showing still other aspects of the AMP 100 depicted in FIG. 1.

In FIG. 3, the server/computing resource 202 is again shown. The server/computing resource 202 is in communication with a machine module 110, as referred to above. The machine module 110 is interfaced to a sensor 302, which provides time-series data relevant to a wind turbine 102 (or another type of asset, for which the wind turbine 102 stands as an example). The sensor 302 may be incorporated in, mounted on, interfaced to or in proximity to the wind turbine/asset 102. The sensor 302 may be of any one of the numerous types of industrial sensors that are currently in use for monitoring industrial installations or other assets. Accordingly, the time-series data stream output from the sensor 102 may represent any one (or more) of various types of parameters or conditions. To make explicit just two of many possible examples, the sensor 102 may be a temperature sensor or may incorporate a strain gauge (not separately shown) to sense strain in one or more components of the wind turbine/asset 102. The machine module 110 may forward the time-series data from the sensor 302 to the server/computing resource 202.

For purposes of one scenario, it will be assumed that the sensor 302 has some processing and communication capabilities, such that a mobile device 206 can be brought into proximity to the sensor 302 to receive a direct feed (via short range radio communication channel 304) of the time-series data from the sensor 302. It is thus assumed that, in the arrangement depicted in FIG. 3, a user (not shown) of the mobile device 206 has brought the mobile device 206 into proximity with the sensor 206 and has requested via the mobile device 206 such a direct, local feed of time-series data from the sensor 206. (In an alternative scenario, the processing and local communication capabilities may be in the machine module 110, and the request for and receipt of time-series data generated by the sensor may be via short-range communications—not shown—between the machine module 110 and the mobile device 206.)

Figure 4:
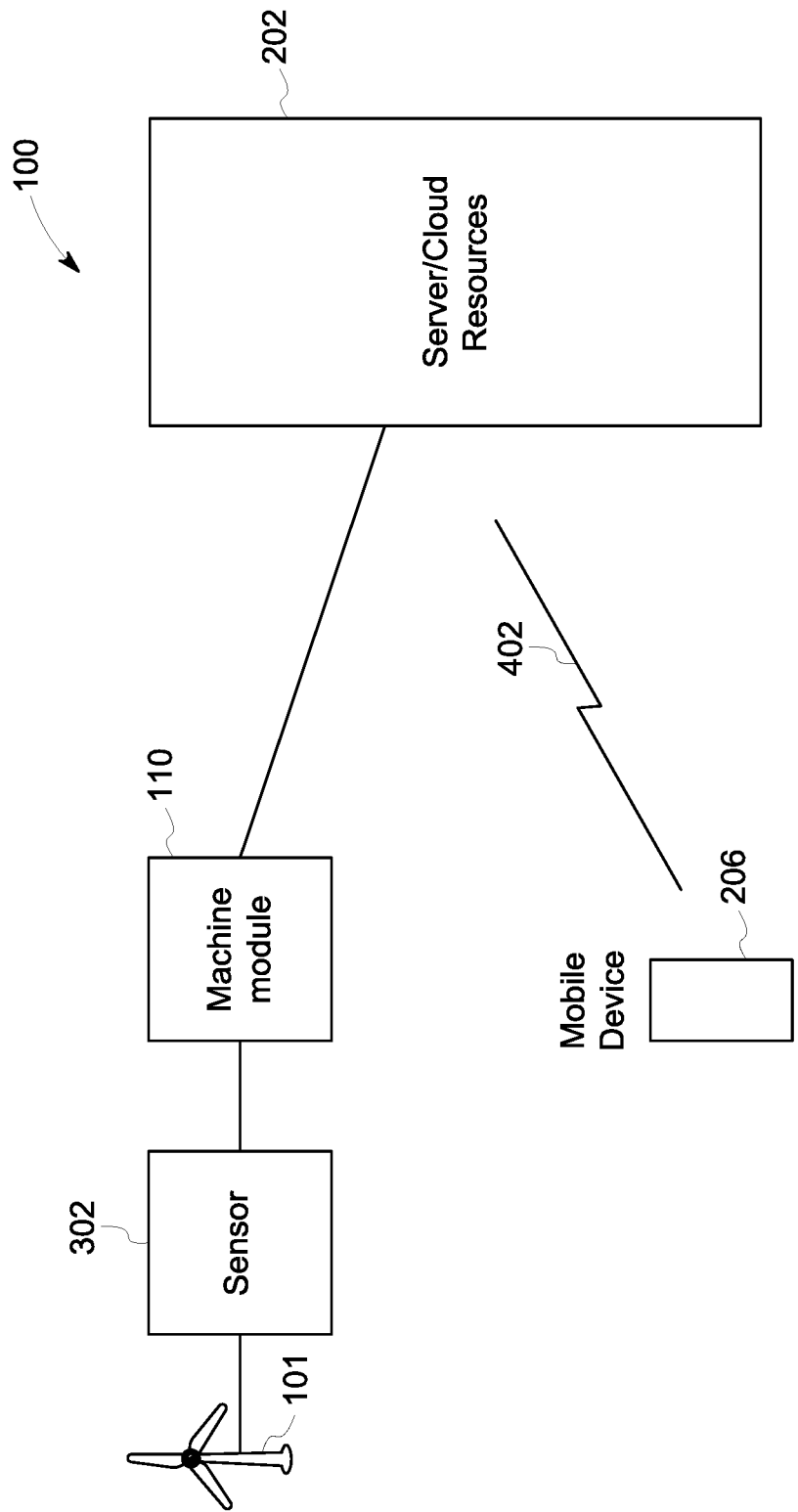

FIG. 4 is a view similar to FIG. 3, but showing a subsequent possible stage of the same scenario. According to this subsequent stage, the user (not shown) of the mobile device 206 has carried the mobile device 206 out of communication range relative to the sensor 302. However, access to the data generated by the sensor 302 is maintained for the mobile device 206, because the server/computing resource 202 now relays the sensor data (in converted form) to the mobile device 206 via a communication channel 402. It will be appreciated that the communication channel 402 may have a mobile telecommunication system (not separately shown) as one of its constituent portions.

Figure 5:
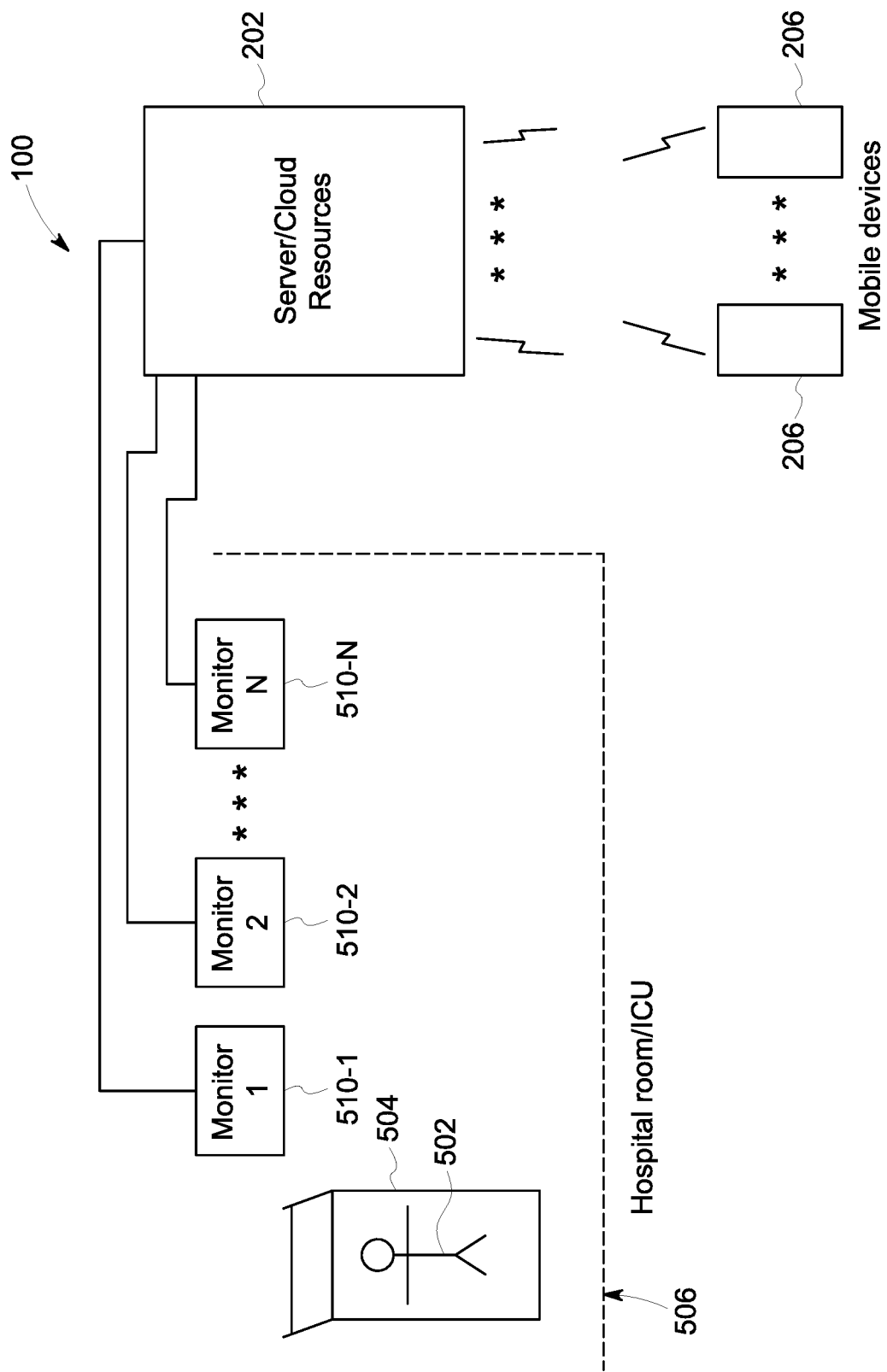

FIG. 5 is a high level block diagram showing still further aspects of the AMP 100 depicted in FIG. 1. In particular FIG. 5 schematically illustrates aspects of a medical example briefly discussed above. A patient 502 is shown occupying a bed 504 in a hospital room, or ICU (intensive care unit) bay 506. Various medical monitoring devices 510-1 through 510-N are located in the room/bay 506. The monitoring devices 510 are sensing vital signs and/or other aspects of the patient's medical/physical/physiological condition and generating time-series data accordingly. To give just a limited set of examples, the monitoring devices 510 may be generating heartrate and/or blood pressure data with respect to the patient 502. The time-series data may be uploaded from the monitoring devices 510 to the server/computing resource 202. The server/computing resource 202 may distribute the data (in converted form) to mobile devices 206 carried by medical professionals (not shown) responsible for caring for the patient 502. As will be understood from subsequent discussion, the server/computing resource 202 may distribute the patient monitor data to the mobile devices 206 in chunk form, with index marks in the distributed data. The index marks may include alarms/alerts/annotation, as described below.

Figure 6:
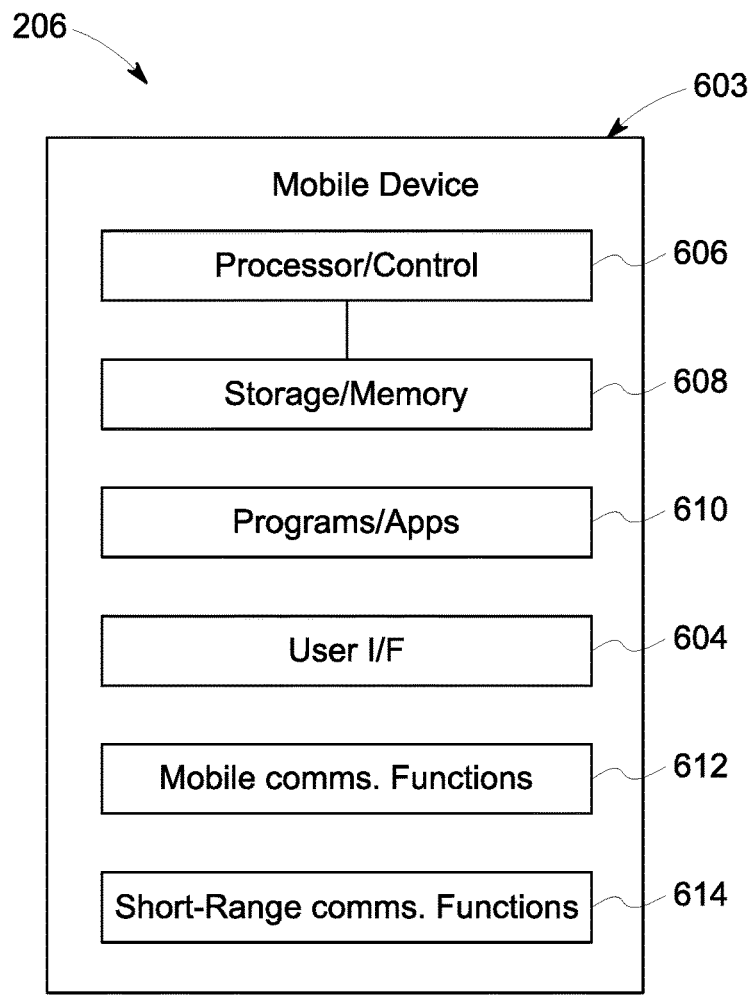
FIG. 6 is a block diagram of a typical mobile device such as those shown in FIGS. 2-5.

FIG. 6 is a block diagram of a typical mobile device 206 such as those shown in FIGS. 2-5.

The mobile device 206 may include a housing 603. In many embodiments, the front of the housing 603 is predominantly constituted by a touchscreen (not separately shown), which is a key element of the user interface 604 of the mobile device 206.

The mobile device 206 further includes a mobile processor/control circuit 606, which is contained within the housing 603. Also included in the mobile device 206 is a storage/memory device or devices (reference numeral 608). The storage/memory devices 608 are in communication with the processor/control circuit 606 and may contain program instructions to control the processor/control circuit 606 to manage and perform various functions of the mobile device 206. In an example the program instructions may, at least in part, contain one or more mobile application programs ("apps") represented at block 610 in FIG. 6, and may, along with other programs, in practice be stored in block 608, to program the processor/control circuit 606.)

As is typical for mobile devices, the mobile device 206 may include mobile communications functions as represented by block 612. The mobile communications functions may include voice and data communications via a mobile communication network with which the mobile device 206 is registered or with which it has been associated. Further, the mobile device 206 may also include capabilities (block 614) for one or more different types of short-range communication (e.g., WiFi, Bluetooth, NFC, etc.).

From the foregoing discussion, it will be appreciated that the blocks depicted in FIG. 6 as components of the mobile device 206 may in effect overlap with each other, and/or there may be functional connections among the blocks which are not explicitly shown in the drawing. It may also be assumed that, like a typical smartphone or tablet computer, the mobile device 206 may include a rechargeable battery (not shown) that is contained within the housing 603 and that provides electrical power to the active components of the mobile device 206.

While the mobile device 606 may be embodied as a smartphone or tablet computer, other hardware and form factor profiles may characterize the mobile device 206. For example, the mobile device may be embodied as a mobile terminal of one of the types issued by enterprises to their traveling technicians, delivery personnel, etc. Such a mobile terminal may feature, for example, a specially configured keypad/touchpad, tailored to suit the mission of the individuals to whom the terminal is issued. In the case of a mobile terminal issued to a technician, the mobile terminal may include relevant test equipment components, etc.

Figure 7:
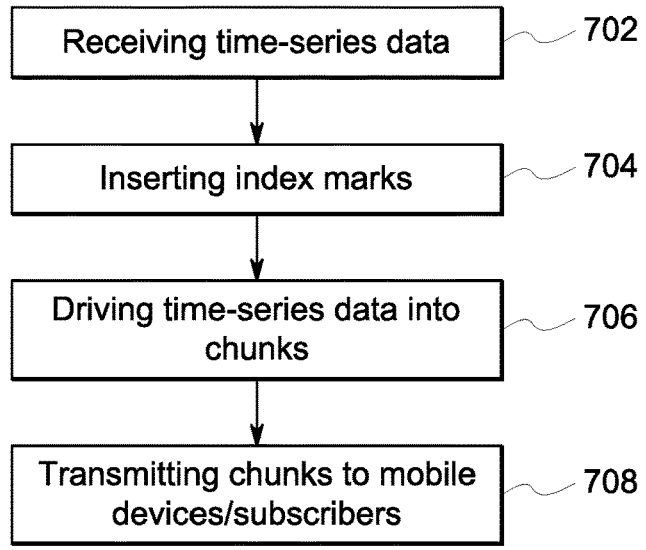
FIGS. 7, 8, 9, 10, 11 and 12 are flow charts that illustrate processes performed according to some embodiments.

FIG. 7 is a high-level flow chart that illustrates a process that may be performed in accordance with teachings of this disclosure.

At 702, the server/computing resource 202 may receive a stream of time-series data from a sensor or machine module or another asset in the AMP 100.

At 704, the server/computing resource 202 may insert one or more index marks into the stream of time-series data, as stored in the server/computing resource 202. In an example, the server/computing resource 202 may machine-read the time-series data as it is received to detect events represented by the time-series data. For example, the values of a parameter represented by the time-series data may change so as to cross a threshold; the crossing of the threshold may signify an event that may be, for example, the emergence of an unsatisfactory or hazardous condition in a system asset, in the medical condition of a patient, etc. For example, the detected event may be the existence of an excessively high pressure, an excessively low pressure, an excessively high temperature, an excessively low temperature, an excessive degree of strain, an excessively high rotational velocity, an excessively low rotational velocity, an excessively high linear velocity, an excessively low linear velocity, a halt in operation, an excessively high heart rate, an excessively low heart rate, an excessively high blood pressure, an excessively low blood pressure, an excessively high body temperature, an excessively low body temperature, an excessive rate of change in a parameter value, etc. The index mark or marks may be indicative of the detected event and may be inserted in a point in the time-series data at or near parameter data that evidences the detected event. In an example, the server/computing resource 202 may undertake a higher-level and/or multifactor analysis to detect an event from one or more streams of time-series data.

Index marks may also be generated by or with other devices (e.g., mobile devices that receive the time-series data from the server/computing resource 202) and may be sent to the server/computing resource 202 for insertion into the stream of time-series data. Moreover, the server/computing resource 202 may generate index marks for insertion into the time-series data stream in response to signals received from a mobile device 206 or other devices that receive the time-series data from the server/computing resource 202.

At 706 in FIG. 7, the server/computing resource 202 divides the time-series data into chunks. One or more of the chunks includes one or more index marks, such as those referred to above. In an example, and without limitation, each chunk may contain 30 seconds' worth of time-series data. The communication bandwidth between the server/computing resource 202 and the mobile device 206 may be such that it takes less than 30 seconds to transmit a chunk of data. The server/computing resource 202 may include multiple (e.g. a large number of) data communication ports so as to simultaneously transmit chunked time-series data (e.g., from numerous streams) to numerous mobile devices 206. For a given stream of data, the server/computing resource 202 may simultaneously transmit different chunks from the data stream to different mobile devices 206.

At 708, the server/computing resource 202 transmits the chunks of time-series data to one or more of the mobile devices 206.

In an example, each mobile device 206 may, for a given data stream, cache a certain quantity (say, five minutes' worth) of data that it receives from the server/computing resource 202. The mobile device 206 may have capabilities for skipping, replaying and/or sharing (i.e., transmitting to another device) portions of the cached time-series data. If sharing is implemented, it may occur via peer-to-peer communications and/or by relay via the server/computing resource 202.

Figure 8:
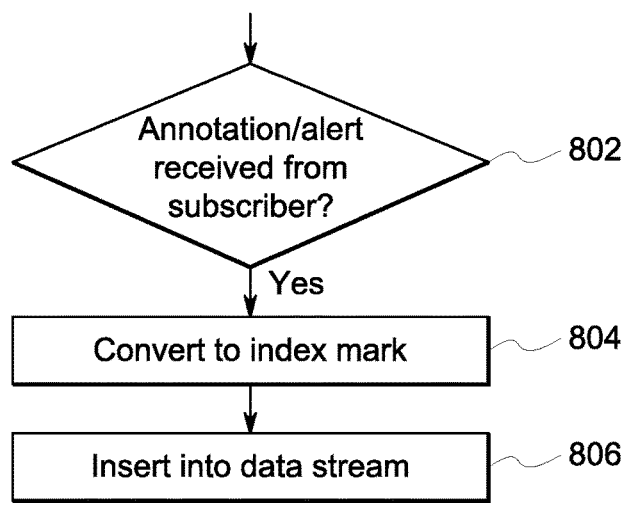

FIG. 8 is a flow chart that illustrates a process that may be performed in accordance with teachings of the present disclosure; FIG. 8 illustrates some details of the process of FIG. 7.

At a decision block 802 in FIG. 8, the server/computing resource 202 determines whether it has received an alert or an annotation from a mobile device 206 that is receiving time-series data from the server/computing resource 202. The annotation or alert may be automatically generated by the mobile device 206 in response to an analysis of the time-series data performed by the mobile device 206. Alternatively, a user of the mobile device may have manually entered an annotation into the mobile device 206 (via the user interface thereof) for transmission from the mobile device 206 to the server/computing resource 202. In an example, the user of the mobile device 206 may be observing the parameter values represented in the time-series data and may have noted some cause for concern. The user may also know that another individual (called "Chris Brown") is also receiving the time-series data from the server/computing resource 202 via his/her mobile device 206. Accordingly, the first user may compose an annotation such as, "Chris, please keep an eye on the rotor strain parameter for wind turbine A35." The annotation may be sent from the first user's mobile device 206 to the server/computing resource 202. As will be seen, the annotation may then be incorporated in the time-series data sent to Chris Brown's mobile device 206.

Referring again to FIG. 8, if a positive determination is made at decision block 802 (i.e., if the server/computing resource 202 determines that it has received an annotation or alert pertinent to one of the feeds of time-series data that it is receiving and relaying), then block 804 may follow decision block 802. At block 804, the server/computing resource 202 converts the annotation or alert into an index mark suitable for insertion into the time-series data. Then, at 806, the server/computing resource 202 inserts the index mark into the time-series data stream as stored in the server/computing resource 202.

Figure 9:
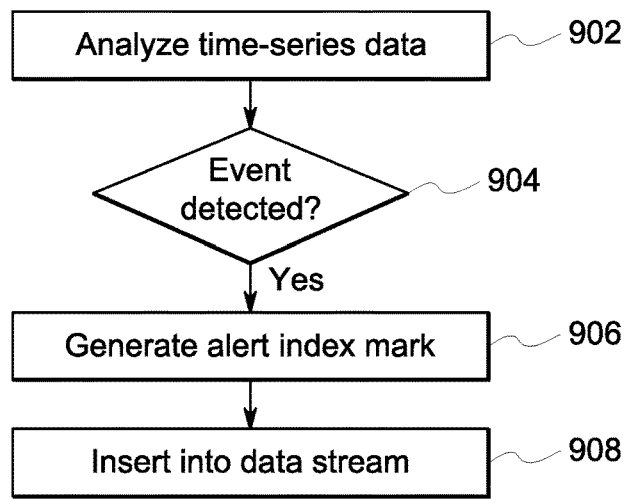

FIG. 9 is a flow chart that illustrates a process that may be performed in accordance with teachings of the present disclosure; FIG. 9 illustrates some details of the process of FIG. 7.

At 902 in FIG. 9, the server/computing resource 202 analyzes the parameter values contained in the time-series data. In an example, the server/computing resource 202 may analyze the data received from a single source or may co-analyze time-series data from two or more sources.

A decision block 904 may follow block 902. At decision block 904, the server/computing resource 202 may determine whether the analysis at 902 has indicated that an event is represented by the time-series data analyzed at 902. If so, then block 906 may follow decision block 904. At block 906, the server/computing resource 202 may generate an index mark that indicates an alert that corresponds to the detected event. Then, at block 908, the server/computing resource 202 may insert the index mark into the time-series data as stored in the server/computing resource 202. The index mark may be inserted at a point in the data stream associated with the detected event.

With processes as described in connection with FIGS. 7-9, the server/computing resource 202 may provide an enhanced time-series data feed to subscribing mobile devices 206. The data feed may indicate analysis/event detection that occurs by either or both of the server/computing resource 202 or via distributed processing analysis/human insight at subscribing mobile devices 206.

Figure 10:
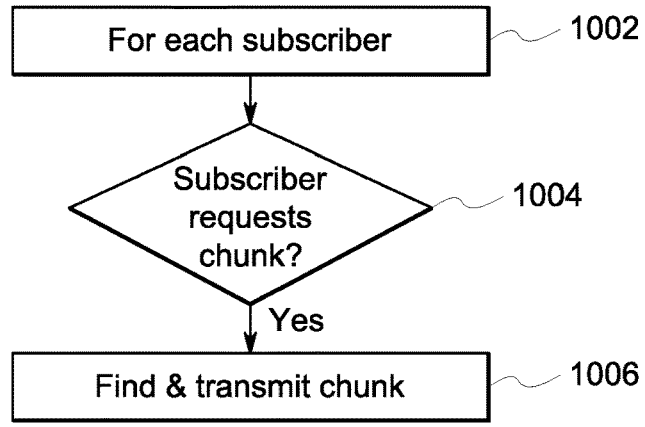

FIG. 10 is a flow chart that illustrates a process that may be performed in accordance with teachings of the present disclosure; FIG. 10 illustrates some details of the process of FIG. 7.

FIG. 10 is premised on the assumption that various mobile devices 206 are established as "subscribers" assigned (or having requested) to receive one or more specific feeds of time-series data from the server/computing resource 202. It is also assumed that each subscriber mobile device 206 knows the sequence number of the most recent chunk of data it has received for a given feed of time-series data to which it is subscribed. It is also assumed that the mobile device knows whether or not it currently has data communication connectivity available by which it may receive chunks of data from the server/computing resource 202.

Block 1002 in FIG. 10 is indicative that the subsequent process steps shown in FIG. 10 are performed with respect to each subscribing mobile device 206 that receives chunk-wise data feeds from the server/computing resource 202.

At decision block 1004, the server/computing resource 202 determines whether a particular subscriber mobile device 206 has requested a chunk of time-series data for a particular time-series data feed to which the mobile device 206 is subscribed. If so, then block 1006 may follow decision block 1004.

In connection with blocks 1004 and 1006, it may be assumed that a request for a chunk contains parameters such as an identifier/address for the subscriber mobile device in question, an identifier for the particular time-series data feed in question, and a chunk sequence number that identifies the most recent chunk from that feed that the mobile device has already received. Based on this information in the request, and as indicated at block 1006, the server/computing resource 202 may find the next chunk of time-series data as requested by the subscriber mobile device. The "next" chunk may be understood to be the oldest chunk (in terms of the time when the data was generated) following the last chunk received as identified in the request from the subscriber mobile device.

In another example, the request from the subscriber mobile device may specify a more recent chunk of data that it wishes to receive instead of the oldest chunk not previously received. For example, if the mobile device has been "off the air" for an extended period of time, it may request that the server/computing resource 202 only go back a limited period of time (say, five minutes) in fetching the next chunk to be transmitted to the mobile device.

Block 1006 represents the server/computing resource 202 transmitting the requested chunk to the mobile device in addition to representing the finding of the requested chunk by the server/computing resource 202.

Figure 11:
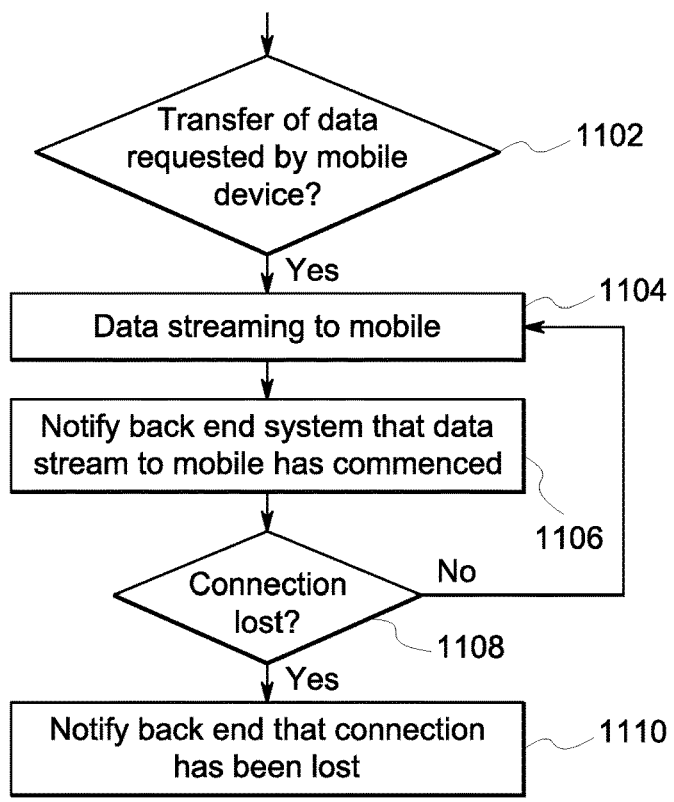

FIG. 11 is a flow chart that illustrates a process that may be performed in accordance with teachings of the present disclosure; FIG. 11 illustrates some details of the process of FIG. 7 and is also pertinent to the scenario shown in FIGS. 3 and 4.

At decision block 1102 in FIG. 11, it is determined whether the mobile device 206 (FIG. 3) has requested a feed of time-series data from the sensor 302 (or from the machine module 110, as the case may be). If such a request is made, then block 1104 may follow decision block 1102. At block 1104, data streaming occurs from the sensor 302 (or machine module 110) to the mobile device 206. The request at 1102 and the data streaming at 1104 may occur over a short range data connection, such as via WiFi. Block 1106 may occur in parallel with block 1104. At block 1106, the mobile device 206 (or the sensor 302/machine module 110) may notify the server/computing resource 202 that the local data streaming at 1104 is taking place.

Decision block 1108 may follow block 1106. At decision block 1108, the mobile device 206 (or the sensor 302/machine module 110) may detect that the short range data connection employed at 1108 has been broken. This may occur, for example, as a result of the mobile device 206 having been carried out of range for the short range data connection. Such a condition is illustrated, for example, in FIG. 4.

If a negative determination occurs at decision block 1108 (i.e., if the local data connection has not been lost), then the process of FIG. 11 may loop back to block 1104. Otherwise, the process of FIG. 11 may advance from decision block 1108 to block 1110. At block 1110, the mobile device 206 (or one of the other local devices referred to above) may notify the server/computing resource 202 that the mobile device is no longer receiving the data feed from the sensor 302 (or the machine module 110, as the case may be).

Figure 12:
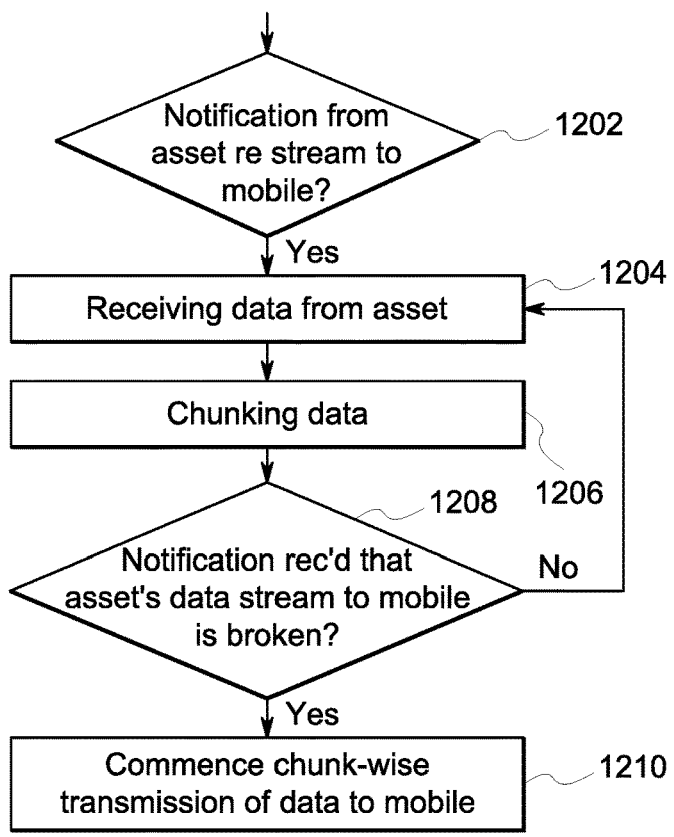

FIG. 12 is a flow chart that illustrates a process that may be performed in accordance with teachings of the present disclosure; FIG. 12 illustrates some details of the process of FIG. 7 and can be considered a companion to FIG. 11, in illustrating how the scenario at FIGS. 3 and 4 may be reflected by processing at the server/computing resource 202.

At decision block 1202 in FIG. 12, the server/computing resource 202 determines whether it has received a notification (e.g. per block 1106, FIG. 11) that the mobile device is receiving a local time-series data feed from the sensor 302 or the machine module 110, as the case may be. If such a notification is received, then the server/computing resource 202 may start receiving (block 1204) and storing a parallel data feed of the time-series data that the mobile device 206 is receiving. As will be seen, this sets up the server/computing resource 202 to serve as a back-up source for the data feed if the local data connection to the mobile device 206 fails or is broken.

Block 1206 may follow block 1204 in the process of FIG. 12. At block 1206, the server/computing resource 202 may proceed to convert the stored time-series data received at 1204 into chunks suitable for transmission to the mobile device 206. This may occur, for example, in a manner suitable for fulfilling the process step 706 in FIG. 7. In an example, insertion of index marks may also occur prior to chunking, as discussed above in connection with FIG. 7.

Continuing to refer to FIG. 12, decision block 1208 may follow block 1206 in the process of FIG. 12. At decision block 1208, the server/computing resource 202 may determine whether it has received a notification (e.g., per block 1110 in FIG. 11), that the mobile device is no longer receiving the local feed of time-series data from the sensor 302 or machine module 110, as the case may be.

If a negative result occurs at decision block 1206 (i.e., no such notification is received), then the process of FIG. 12 may loop back from decision block 1206 to blocks 1204 and 1206. However, if a positive determination is made at decision block 1206 (i.e., such a notification is received) then block 1210 may follow decision block 1208.

At block 1210, the server/computing resource 202 may begin chunk-wise transmission to the mobile device 206 of the time-series data that was previously being received by the mobile device 206 via a local data connection. It will be appreciated that to support this process step, the server/computing resource 202 may continue to receive and convert (to chunks) the time-series data from the sensor 302. In an example, the chunks of time-series data are transmitted from the server/computing resource 202 to the mobile device 206 commencing with a point in time in the data stream at which the mobile device 206 ceased receiving the local data stream of time-series data.

In an example, instead of or in addition to sending the full data stream chunk-wise to a mobile device 206, the server/computing resource 202 may summarize the contents of portions of the data stream and send the resulting summaries to the mobile device 206. In an example, one mobile device/subscriber 206 may opt to receive half or a third (e.g., every second or third item of time-series data) or another fraction of the data stream, while another mobile device 206 may opt to receive the full data stream or a different fraction thereof.

In an example, the respective arrangements between the mobile devices 206 and the server/computing resource 202 may be "tuned" in that more or less data analysis occurs at the server/computing resource 202 and/or more or less data analysis occurs at the mobile devices 206. The "tuning" may be on a mobile-device-by-mobile-device basis. Results of data analysis by mobile devices 206 may be uploaded to the server/computing resource 202 and/or shared with other mobile devices 206 directly or via the server/computing resource 202.

Figure 13:
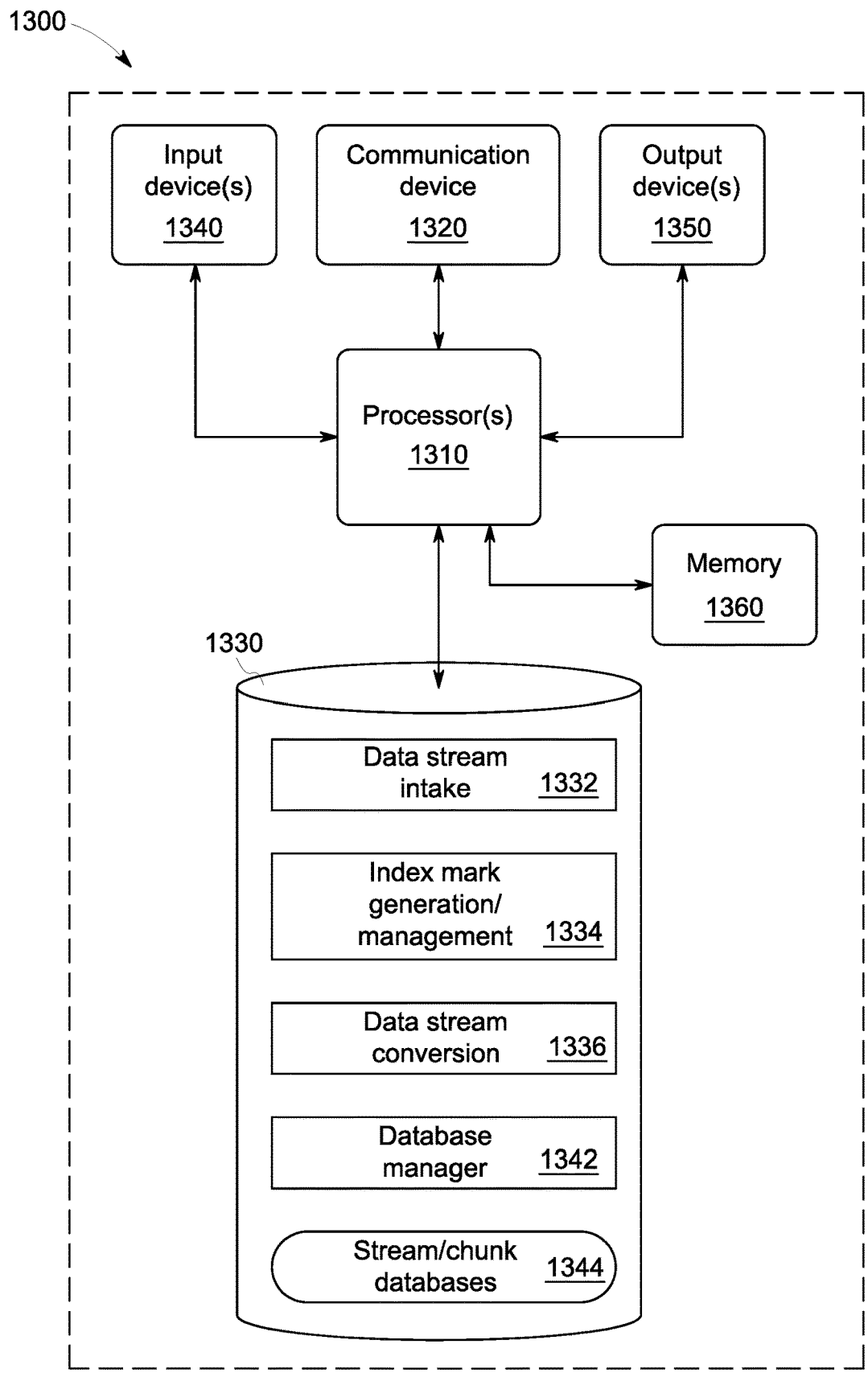
FIG. 13 is a block diagram of a computing system according to some embodiments.

Computer 1300 shown in FIG. 13 is an example hardware-oriented representation of the server/computing resource 202 shown in FIGS. 2-5.

Referring to FIG. 13, computer 1300 includes one or more processors 1310 operatively coupled to communication device 1320, data storage device 1330, one or more input devices 1340, one or more output devices 1350 and memory 1360. Communication device 1320 may facilitate communication with external devices, such as data generating devices and/or mobile devices that receive data from computer 1300. Input device(s) 1340 may include, for example, a keyboard, a keypad, a mouse or other pointing device, a microphone, knob or a switch, an infra-red (IR) port, a docking station, and/or a touch screen. Input device(s) 1040 may be used, for example, to enter information into the computer 1300. Output device(s) 1350 may include, for example, a display (e.g., a display screen), a speaker, and/or a printer.

Data storage device 1330 may include any appropriate persistent (i.e., non-transitory) storage device, including combinations of magnetic storage devices (e.g., magnetic tape, hard disk drives and flash memory), optical storage devices, Read Only Memory (ROM) devices, etc., while memory 1360 may include Random Access Memory (RAM). The data storage device 1330 and the memory 1360 may be in communication with each other and/or with the processor(s) 1310.

Data storage device 1330 may store software programs that include program code executed by processor(s) 1310 to cause computer 1300 to perform any one or more of the processes described herein. Embodiments are not limited to execution of these processes by a single apparatus. For example, the data storage device 1330 may store data stream intake software 1332.

Continuing to refer to FIG. 13, data storage device 1330 may also store index mark generation and management software 1334.

In addition, data storage device 1330 may store a software program 1336, which converts streams of time-series data into data chunks.

Also, data storage device 1330 may store a database manager program 1342 and one or more time-series/chunk databases 1344, which may be processed or stored in the computer 1300. Data storage device 1330 may store other data and other program code for providing additional functionality and/or which are necessary for operation of computer 1300, such as device drivers, operating system files, etc.

A technical effect is to improve access to AMP system data for mobile devices.

The foregoing diagrams represent logical architectures for describing processes according to some embodiments, and actual implementations may include more or different components arranged in other manners. Other topologies may be used in conjunction with other embodiments. Moreover, each system described herein may be implemented by any number of devices in communication via any number of other public and/or private networks. Two or more of such computing devices may be located remote from one another and may communicate with one another via any known manner of network(s) and/or a dedicated connection. Each device may include any number of hardware and/or software elements suitable to provide the functions described herein as well as any other functions. For example, any computing device used in an implementation of some embodiments may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Flash drive, magnetic tape, and solid state Random Access Memory (RAM) or Read Only Memory (ROM) storage units. Embodiments are therefore not limited to any specific combination of hardware and software.

The term "data generating device" as used herein and in the appended claims, includes but is not limited to sensors and monitoring devices, including medical monitoring devices.

The flow charts and descriptions thereof herein should not be understood to prescribe a fixed order of performing the method steps described therein. Rather the method steps may be performed in any order that is practicable, including simultaneous performance of steps.

Embodiments described herein are solely for the purpose of illustration. A person of ordinary skill in the relevant art may recognize other embodiments may be practiced with modifications and alterations to that described above.

What is claimed is:

1. A method comprising:
receiving, in a computer system, an indication that a data generating device is supplying time-series data to a mobile device;
receiving, in the computer system, a stream of time-series data from the data generating device;
receiving, in the computer system, an indication that communication has ceased between the data generating device and the mobile device at a certain point in the stream of time-series data;
converting, in the computer system, the stream of time-series data into a sequence of data chunks; and
transmitting, from the computer system, said stream of time-series data to said mobile device starting from said certain point in the stream of time-series data, said transmitting occurring in a sequence of one or more selected chunks taken from the certain point, where each selected chunk is transmitted by the computer system to the mobile device in response to an indication by the mobile device that it is available to receive a next chunk of said selected chunks.

2. The method of claim 1, wherein the data generating device includes a sensor.

3. The method of claim 2, wherein the sensor is associated with a mechanical device.

4. The method of claim 3, wherein the data generating device includes a plurality of sensors associated with the mechanical device.

5. The method of claim 2, wherein the sensor is a temperature sensor.

* * * * *